United States Patent [19]
Jaslow et al.

[11] Patent Number: 6,004,195
[45] Date of Patent: Dec. 21, 1999

[54] CROWN AND BRIDGE CLAMP AND FINISHING SYSTEM

[76] Inventors: Saul Jaslow; Lewis H. Jaslow, both of P. O. Box 1882, Beverly Hills, Calif. 90213

[21] Appl. No.: 08/861,417

[22] Filed: May 21, 1997

[51] Int. Cl.$^6$ .................................................. B24B 41/06
[52] U.S. Cl. ........................................... 451/391; 451/404
[58] Field of Search ..................................... 451/364, 403, 451/391, 404

[56] References Cited

U.S. PATENT DOCUMENTS 4,475,370  10/1984  Stark et al. ............................ 451/89 X
5,688,533  11/1997  Berger.

*Primary Examiner*—Timothy V. Eley

[57] ABSTRACT

A support system enabling the dental technician an easy and concise method of grinding dental castings including a pedestal for supporting the underside, an outer arm which supports the outside surface of the casting, both being variably shaped to adapt to the wide variety of their shapes and sizes. The base which connects both the outer arm and pedestal provides movement for proper positioning of the dental casting.

10 Claims, 2 Drawing Sheets

CROWN AND BRIDGE CLAMP AND FINISHING SYSTEM

BACKGROUND—FIELD OF INVENTION

This invention relates to the finishing of dental castings, specifically to the improved process of holding these castings.

BACKGROUND ART

Dental laboratories and dentists have been faced with many problems germain to the process of finishing crowns and ceramic castings. The major problem with this process is an efficient way to hold the casting so that enough pressure could be applied to grind off the remainder of the sprue and excess metal. The sprue is excess metal left from the casting process. Presently, the proper way of grinding a dental casting is accomplished by being held in one hand while grinding excess metal with the other. The excess metal as it is ground away, generates heat. The heat must either be tolerated by the person holding the casting in his or her fingers or drenched in water. The more pressure applied to grinding the faster the process and more heat. The human hand can only withstand a moderate amount of pressure and heat at one time.

To solve this problem a system must be developed which can accommodate the many variations in shape and size of castings. Our invention provides the user with an efficient way of processing a wide range of castings. No need to hold back on pressure, no reason to have excessive heat on fingers and hands thereby accelerating speed and production.

SUMMARY OF THE INVENTION

To grind the surface of a dental casting for preparation of its proper shape and thickness. This preparation is accomplished by supporting the under side and the outer surface with a pedestal and upper arm using primarily one hand during this grinding process. Both the pedestal and the upper arm are variably shaped to adapt to the many shapes of dental castings. As the arm, casting, and pedestal are properly positioned, a safe grinding process is created. Adjustments can be made, enabling access to different sides of the casting. In addition to the improved grinding speed and efficiency this machine reduces steps in this process thus creating a more cost effective product.

This inventive concept can also be a pencil like single hand held unit, still having the choice of the upper and or lower support while grinding with one hand and holding with the other, yet no heat on fingers and hands.

BRIEF DESCRIPTION OF THE DRAWINGS

FIG. 7 Whereas;

FIG. 7A is a side and top view of a typical support arm;

FIG. 7B is a top view of a support arm with a smaller tip;

FIG. 7C is a top view of an adjustable circumferential support arm tip;

FIG. 7D is a top view of a non-adjustable circumferential support arm tip;

DESCRIPTION OF THE PREFERRED EMBODIMENT

Figure 1:
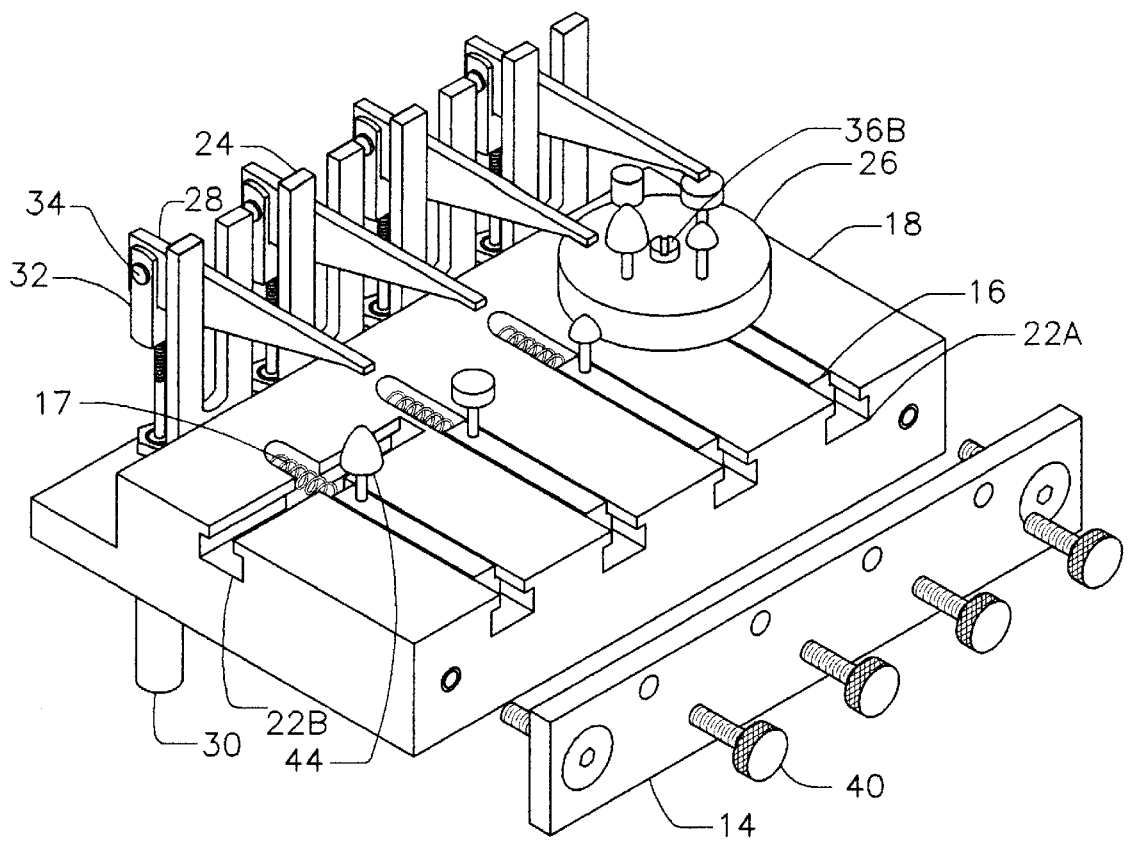
FIG. 1 is a perspective view of a multiple unit system therefor above and to the left of the apparatus.
Figure 2:
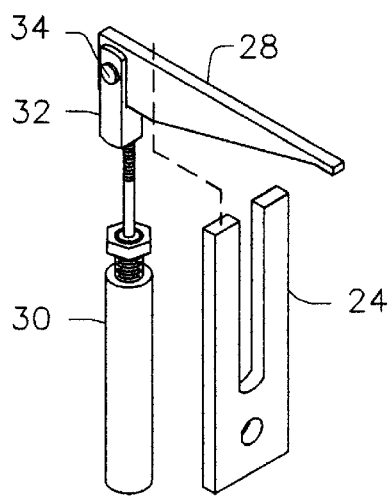
FIG. 2 is a perspective view of a support arm with a support arm guide, and an air cylinder.
Figure 3:
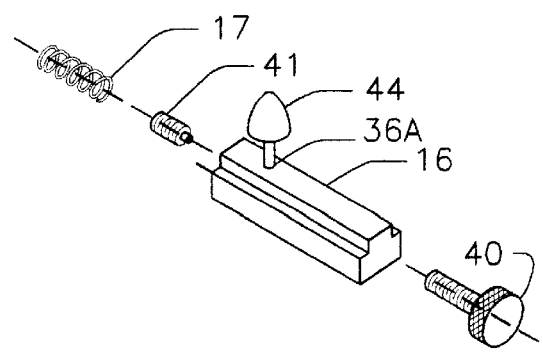
FIG. 3 is an exploded view of the T-bar, pedestal, ball plunger, tension spring, and adjustment knob system.

A typical embodiment of he Crown and Bridge Clamp and Finishinig System of the present invention is illustrated in (FIG. 1.) perspective view. The base 18 can have several T-slots 22A and 22B. Each T-slot has a T-bar 16, in which a pedestal 60, is inserted into the T-bar interacting with a ball plunger 41 and pedestal indent 48 The pedestal with the T-bar is adjusted by the adjustment knob 40 having back and forth movement by way of tension caused by spring 17 and the T-bar cover plate 14. See (FIG. 3) exploded view of the T-bar 16, adjustment knob 40, pedestal 44, ball plunger 41, and spring 17. Also in (FIG. 1) connected to the base 18 is an upper arm support guide 28 demonstrated in (FIG. 2). (FIG. 1) further demonstrates a rotary pedestal holder 26 which is used for easy selection of several pedestals at one time. The T-slot 22B (FIG. 1.) on the left side of the system base has a separate purpose. This purpose is to give more than one unit bridges the ability of support by way of side support of the bridge. For large situations this T-slot would have the same parts as another T-slot except it would have side movement.

For proper positioning of the outer support arm 28, (FIG. 2.) a guide is used 24. This guide prevents unnecessary side to side movement. The outer support arm is secured to a clevis 32 by a clevis pin which in turn is secured to an air cylinder, toggle clamp, electric solenoid, or other means. These items, outer support arm 20, clevis pin 34, clevis 32, air cylinder 30, and outer support arm guide 24, are all supported to the rear of the system base 18.

In an exploded view (FIG. 3.) an adjustment knob 40 either pushes or releases the position of the T-bar 16 which in turn places the pedestal head 44 in proper position with the outer support arm 28 (FIG. 2.) giving access of different areas of the casting for grinding. In (FIG. 3.) there are two holes, one on top of the T-Bar 36A, and one in the rear of the T-Bar where a ball plunger 41 is inserted. The ball plunger after insertion into the T-bar is slightly intruding into the pedestal hole 36A.

Figure 4:
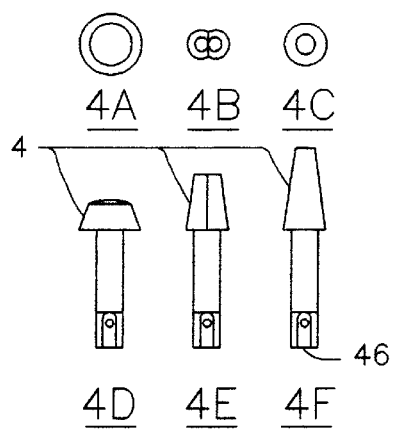
FIG. 4 are front views of the three basic types of pedestals demonstrated as 4D, 4E, and 4F, where 4A, 4B, and 4C are their respective top views.
Figure 5:
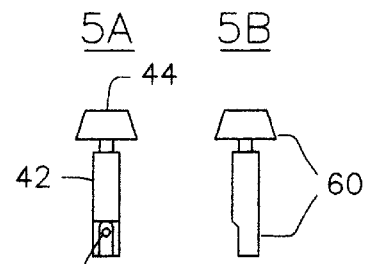
FIG. 5 is a pedestal where 5A is the front, 5B is the side, and 5C is the bottom views of a single sleuth shank.

Note the sleuth way 46 (FIG. 4 and FIG. 5.). As a pedestal is inserted into the T-bar 16 the ball plunger 41 intermingles with the sleuth way eventually snapping into indent 48 (FIG. 5.). or extracted pedestal shank 42. (FIG. 4.) also demonstrates various basic shapes of pedestal heads viewed from top and front. (FIG. 5.) shows the front, side, and bottom view of a typical pedestal, pedestal head 44, shank 42, and pedestal 60 as a unit.

(FIG. 6.) illustrates a pedestal like in (FIG. 5.) except that it has several sleuth ways 46, a sleuth way overplass 62, and a rotation support table 58. These added features allow easy insertion and the ability to rotate the pedestal by way of the ball plunger passing the sleuth way overpass 62, eventually resting under the rotation support table.

Figure 7:
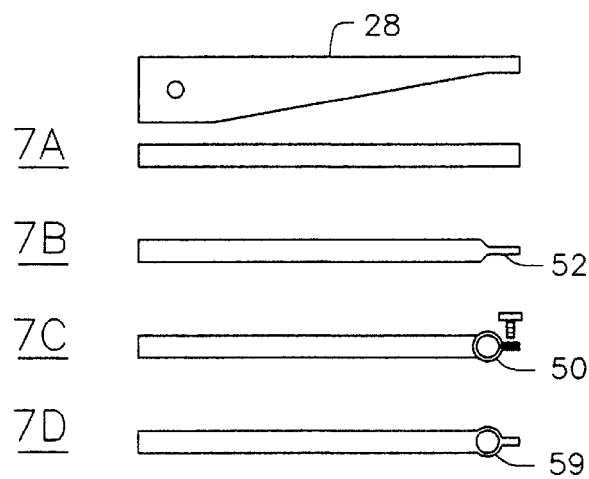

As mentioned in (FIG. 2.), an outer support arm (FIG. 7.) acts as an external support. This support would be on top of or around a crown or coping. The external support arm could also act independently of the pedestal by being a circumferential support arm, encircling and supporting the margin area of a casting. Two basic shapes of support arms are illustrated (FIG. 7.). One is circumferential and the other is not. Many shapes are possible and can be adjustable (FIG. 7C.), to adapt to the vast variety of dental castings.

Figure 8:
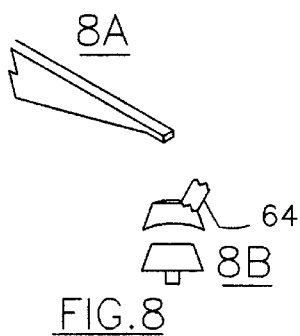
FIG. 8 demonstrates the interaction of the upper support arm, 8A, dental casting, and pedestal 8B, and FIG. 9 are examples of three basic shapes of dental castings for ceramic crowns with, 9A as a molar side view, 9B as a bicuspid front view, 9C as a central front view, each demonstrating the excess sprue remainder. The prior art designation indicates only that which is old is illustrated.
Figure 9:
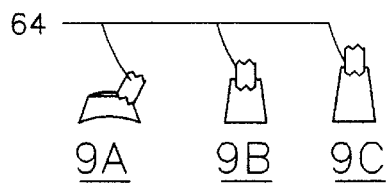

(FIG. 8.) typically an outer support arm 28, coping (FIG. 9A.) with exposed sprue 64, and a typical pedestal head 44, all interacting together demonstrating the system.

Figure 6:
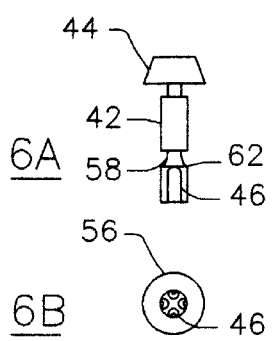
FIG. 6 is a front and bottom view of a multiple sleuth pedestal shank with a rotation support table where 6A is one side, and 6B is the bottom.

Refering back to (FIG. 8.) which demonstrates support for a crown, coping or bridge so that extra pressure could be applied without unwanted movement. With the pedestal 60 and upper arm interacting with a dental casting such as (FIG. 9A.) that unwanted movement while grinding can be eliminated using mostly one hand. The dental technician may customize the pedestal head 44 shape, or mold his or her own by inverting the casting, pouring in a liquid type material like plastic into the casting, then inverting a pedestal shank 42 thus inserting it into the casting and plastic. Once the plastic has hardened the pedestal head is part of the pedestal shank, but not part of the casting. The two parts could be connected or disconnected during the grinding process. While grinding, the technician has a choice of a stationary (FIG. 4.) or moveable pedestal (FIG. 6.). In (FIG. 6.) the pedestal has a rotary support table which a ball plunger (FIG. 3.) 41 supports. The ball plunger is threaded to the rear of a T-Bar, which protrudes into hole 36A. This threaded hole is not demonstrated.

With the many variations of dental castings, three basic shapes are shown (FIG. 9.), each demonstrating excess metal left from the casting channel, the sprue.

Having a system where there is a choice of direction or movement, stationary, backward, forward, side to side, and circular access to the surfaces is quite convenient. Thus the ease in movement allows less hand contact eliminating heat transfer to the fingers. Many times castings are quite small with the sprue on the tip, yet with this system the castings can still be held in a stationary position arid ground to a proper shape and thickness with no heat.

A prefered embodiment has been shown and described and it is to be understood that various other adaptations and modifications may be made within the spirit and scope of the invention without departing from such principles.

We claim:

1. Apparatus for supporting a dental casting during a finishing process comprising:
   a base;
   a pedestal having a variably-shaped head for holding the dental casting, and means for securing the pedestal to the base; and
   means, associated with the base, for holding and laterally adjusting the position of the pedestal relative to said base.

2. The apparatus of claim 1, wherein the pedestal holding and adjusting means comprise:
   the base having at least one elongate T-shaped slot, said T-shaped slot having a front and back end formed in the base, wherein the front end of the T-shaped slot terminates at a first side of the base and the back end of the T-shaped slot terminates prior to a side opposite the first side of the base;
   at least one elongate T-shaped body having a top side with a hole for inserting the pedestal, said at least one T-shaped body located within the at least one T-shaped slot;
   a spring located within the T-shaped slot between the back end of the T-shaped slot and the at least one T-shaped body;
   a ball plunger for engaging the pedestal when said pedestal is inserted in said hole;
   at least one knob, attached to the first side of the base, which is in constant contact with the front side of the at least one T-shaped body for adjusting the position of the T-shaped body.

3. The pedestal of claim 1, further comprising:
   a plate having a plurality of pedestal heads attached to the plate, wherein each pedestal head is variably-shaped respective to each of the other pedestal heads.

4. The apparatus of claim 1, wherein:
   the pedestal head is made of a malleable substance which forms to the dental casting.

5. The apparatus of claim 1, further comprising:
   a support arm attached to the base for holding the dental casting on the pedestal head.

6. The apparatus of claim 5, wherein:
   the support arm is operated by one of the devices selected from the group consisting of:
   manual operation;
   an air cylinder;
   an electrical solenoid;
   hydraulic pressure; and
   a mechanical clamp.

7. Apparatus for supporting a dental casting comprising:
   a base having at least one T-shaped slot, said T-shaped slot having a front and back end formed in the base, wherein the front end of the T-shaped slot terminates at a first side of the base and the back end of the T-shaped slot terminates prior to a side opposite the first side of the base;
   at least one elongate T-shaped body having a top side with a hole for inserting the pedestal, said at least one T-shaped body located within the at least one T-shaped slot;
   a pedestal having a variably-shaped head for holding the dental casting, and means for securing the pedestal to the T-shaped body; and
   a support arm attached to the base for holding the dental casting on the pedestal head.

8. The apparatus of claim 7, wherein:
   the support arm is operated by one of the devices selected from the group consisting of:
   manual operation;
   an air cylinder;
   an electrical solenoid;
   hydraulic pressure; and
   a mechanical clamp.

9. A device for supporting a dental casting comprising:

a rod;

a variably-shaped head, attached to the top of the rod, for holding the dental casting; and means comprising a base for bracing the rod during grinding of the dental casting, said base having means for laterally adjusting the position of the head relative to said base.

10. The device of claim 9, wherein:

the variably-shaped head is made of a malleable substance for forming to the dental casting.

* * * * *